United States Patent [19]

Mullett

[11] Patent Number: 5,121,754
[45] Date of Patent: Jun. 16, 1992

[54] LATERAL DISPLACEMENT PERCUTANEOUSLY INSERTED EPIDURAL LEAD

[75] Inventor: Keith R. Mullett, Minneapolis, Minn.

[73] Assignee: Medtronic, Inc., Minneapolis, Minn.

[21] Appl. No.: 570,439

[22] Filed: Aug. 21, 1990

[51] Int. Cl.$^5$ .............................................. A61N 1/05
[52] U.S. Cl. .................................. 128/786; 128/419 P
[58] Field of Search ...................... 128/786, 785, 419 P

[56] References Cited

U.S. PATENT DOCUMENTS

| | | | |
|---|---|---|---|
| 3,646,940 | 3/1972 | Timm et al. | 128/421 |
| 4,154,247 | 5/1979 | O'Neill | 128/419 P |
| 4,285,347 | 8/1981 | Hess | 128/785 |
| 4,374,527 | 2/1983 | Iversen | 128/786 |
| 4,379,462 | 4/1983 | Borkan et al. | 128/786 |

Primary Examiner—William E. Kamm
Assistant Examiner—Scott M. Getzow
Attorney, Agent, or Firm—Harold R. Patton; Terry L. Wiles; John L. Rooney

[57] ABSTRACT

An insulated electrical lead for coupling the output of a neurological stimulator with the tissue to be stimulated. In most situations, the neurological stimulator is an implantable pulse generator and the tissue to be stimulated is the spinal cord, although other configurations are contemplated. The insulated electrical lead has a sealable connector at the proximal end which couples to the implantable pulse generator. The distal end contains a number of electrodes placed in close proximity to the tissue to be stimulated. A different conductor couples each of the electrodes to the proximal connector. The distal portion of the insulated lead has a deformable sigmoidal shape. The electrodes are spaced along the length of the deformable sigmoidal shape. This causes the electrodes to be displaced laterally so that specific neural tracts in the spinal cord are preferentially stimulated by various combinations of electrode polarity.

14 Claims, 5 Drawing Sheets

5,121,754

LATERAL DISPLACEMENT PERCUTANEOUSLY INSERTED EPIDURAL LEAD

CROSS REFERENCE TO CO-PENDING APPLICATIONS

This application is related to Ser. No. 07/490,065, filed Mar. 7, 1990, entitled "Position-Responsive Neuro Stimulator", assigned to the assignee of the present invention.

BACKGROUND OF THE INVENTION

1. Field of the Invention

The present invention relates generally to chronically implantable tissue stimulators and more particularly relates to insulated leads for chronically implantable tissue stimulators.

2. Description of the Prior Art

Tissue stimulators have been used for some time. Much work has been done in the area of stimulation of the myocardium in artificial cardiac pacing. Insulated leads have been developed to conduct the stimulation signal from the implantable pulse generator to myocardial tissue. Certain lead designs such as taught in U.S. Pat. No. 4,154,247 issued to O'Neill have employed a unique shape to ensure stability of electrode placement.

Implantable pulse generators have also been designed to interact with tissue within the neurological system to produce various desired medical effects. The most common application is the use of such a system to control pain. The PISCES ® implantable spinal cord stimulator system available from Medtronic, Inc. of Minneapolis, Minn. is an example of such a stimulation system.

As with the field of myocardial stimulation, neurological stimulation systems must address the problem of proper electrode placement. U.S. Pat. No. 3,646,940 issued to Timm, et al. is an early example of an electrode system which is positioned by the surgeon and then sutured into place. A positioning scheme more expressly designed for the spinal cord is discussed in U.S. Pat. No. 4,285,347 issued to Hess. The Hess technique employs a shaped protrusion at the distal tip to hold the electrode in position.

The PISCES-SIGMA ® neurological electrode also available from Medtronic, Inc. has a sigmoidal shape to fix electrode position. However, this device, as well as the Hess electrode, have the shaped fixation device proximal to the actual electrode. Therefore, it is primarily the distal tip of the insulated lead which becomes fixed in position A major problem with these prior art leads is that the physician is limited in his ability to acutely and chronically select the site of stimulation within the spinal cord. Currently, this selection is performed at implantation by requiring the surgeon to surgically or percutaneously place the electrode at the exact position to be stimulated.

SUMMARY OF THE INVENTION

The present invention overcomes the disadvantages of the prior art by providing a percutaneously implanted insulated lead for neurological application which laterally positions a plurality of independent electrodes within the spinal cord. The device employs a sigmoidal bend in the distal portion of the insulated lead. A stylet is inserted to straighten the sigmoidal bend during percutaneous insertion. After placement, the stylet is removed and the sigmoidal bend deforms such that it promotes frictional engagement of the entire distal end of the insulated lead within the epidural space. Because the electrodes are dispersed along the sigmoidal shape, they are urged into close proximity with tissue at various lateral positions and, therefore, along various longitudinal tracts of the spinal cord. By individually coupling each electrode to a different switchable output of the pulse generator, the optimal stimulation site can be readily selected.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

FIG. is a schematic view of a patient with a chronically implanted neurological stimulation system employing the present invention.

DETAILED DESCRIPTION OF THE PREFERRED EMBODIMENTS

Figure 1:
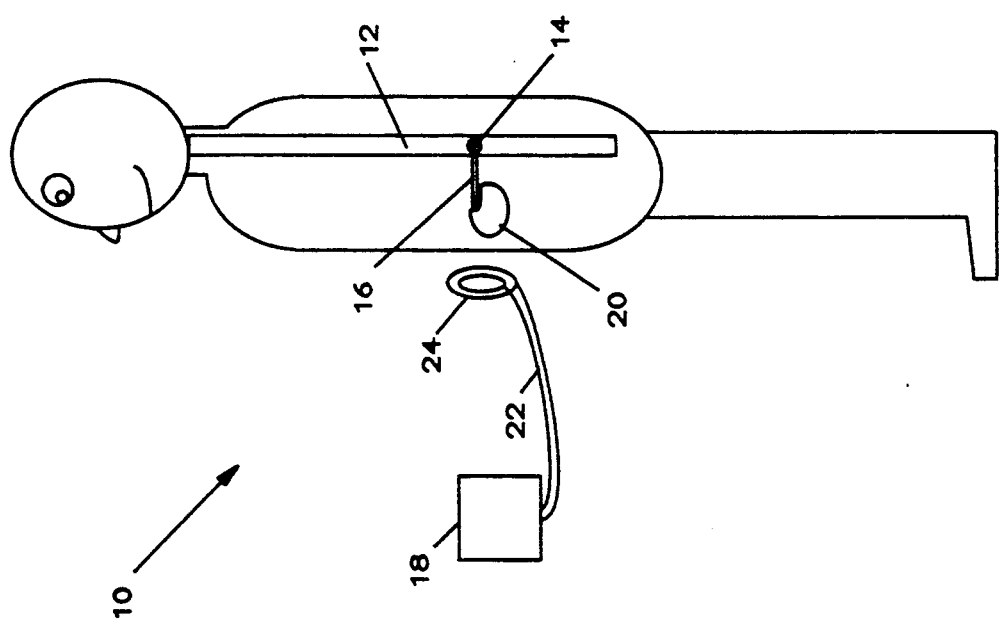

FIG. 1 is a schematic view of patient 10 having an implant of a neurological stimulation system employing the present invention. The preferred system employs programmer 18 which is coupled via conductor 22 to radio frequency antenna 24. This permits attending medical personnel to change various stimulation parameters after implant using the radio frequency communication.

This communication is directed to implantable pulse generator 20. The stimulation pulses are produced by implantable pulse generator 20 which is preferably an ITREL IIR implantable neurological pulse generator available from Medtronic, Inc.

The stimulation pulses produced by implantable neurological pulse generator 20 are coupled to spinal cord 12 using insulated lead 16 of the present invention. The electrodes of insulated lead 16 are located at point 14 of spinal cord 12.

Though the preferred mode employs fully implanted elements, systems employing partially implanted generators and R-F coupling may also practise the present invention.

Figure 2:
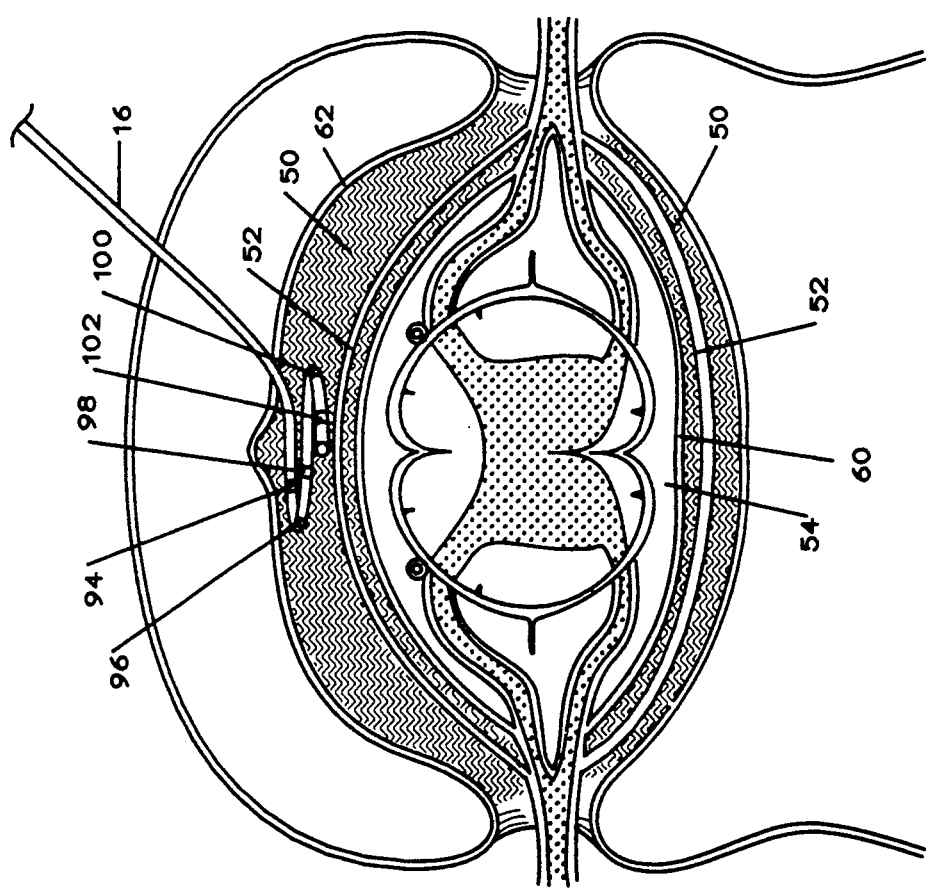
FIG. 2 is a cross sectional view of the spinal cord showing implantation of an insulated lead of the present invention

FIG. 2 is a cross sectional view of spinal cord 12 showing implantation of the distal end of insulated lead 16 at point 14 within epidural space 50. Also shown for purposes of orientation is the subdural space 54 located underneath the dura mater 52 and arachnoid membrane 60.

Figure 3:
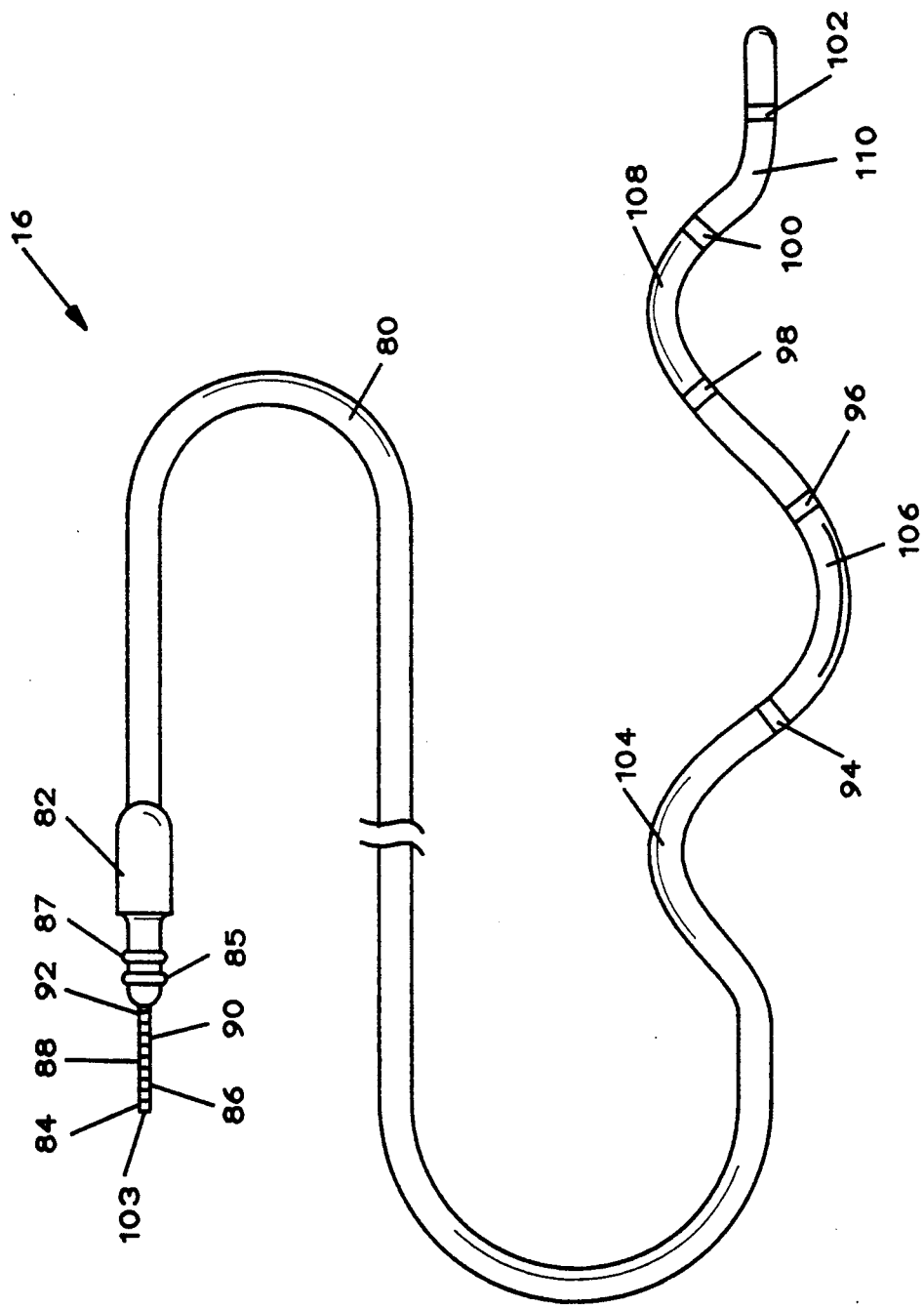
FIG. 3 is a plan view of an insulated neurological lead employing the present invention.

FIG. 3 is a plan view of insulated lead 16 incorporating the present invention. The connector of the proximal end has an insulated and body compatible plug 82 which protrudes from implantable pulse generator 20 after insertion. Proximal to insulated and body-compatible plug 82 are sealing rings 85 and 87. These ensure the complete seal required during chronic implantation. Conductor rings 84, 86, 88, 90, and 92 are mutually insulated and electrically coupled to electrode rings 94, 96, 98, 100, and 102, respectively. The proximal tip contains an aperture 103 of sufficient size to accommodate insertion of a straightening stylet as further described below.

The body of insulated lead 16 contains the conductors which couple the conductor rings to the respective electrode rings. These conductors are mutually insulated. Insulated lead 16 is covered with body-compatible outer sheath 80.

The distal end of insulated lead 16 is characterized by a deformable sigmoidal bend having individual bends 104, 106, and 108. Electrodes 94, 96, 98, 100, and 102 are mutually insulated and interspersed with individual bends 104, 106, and 108 and 110 of the deformable sigmoidal bend.

Figure 4:
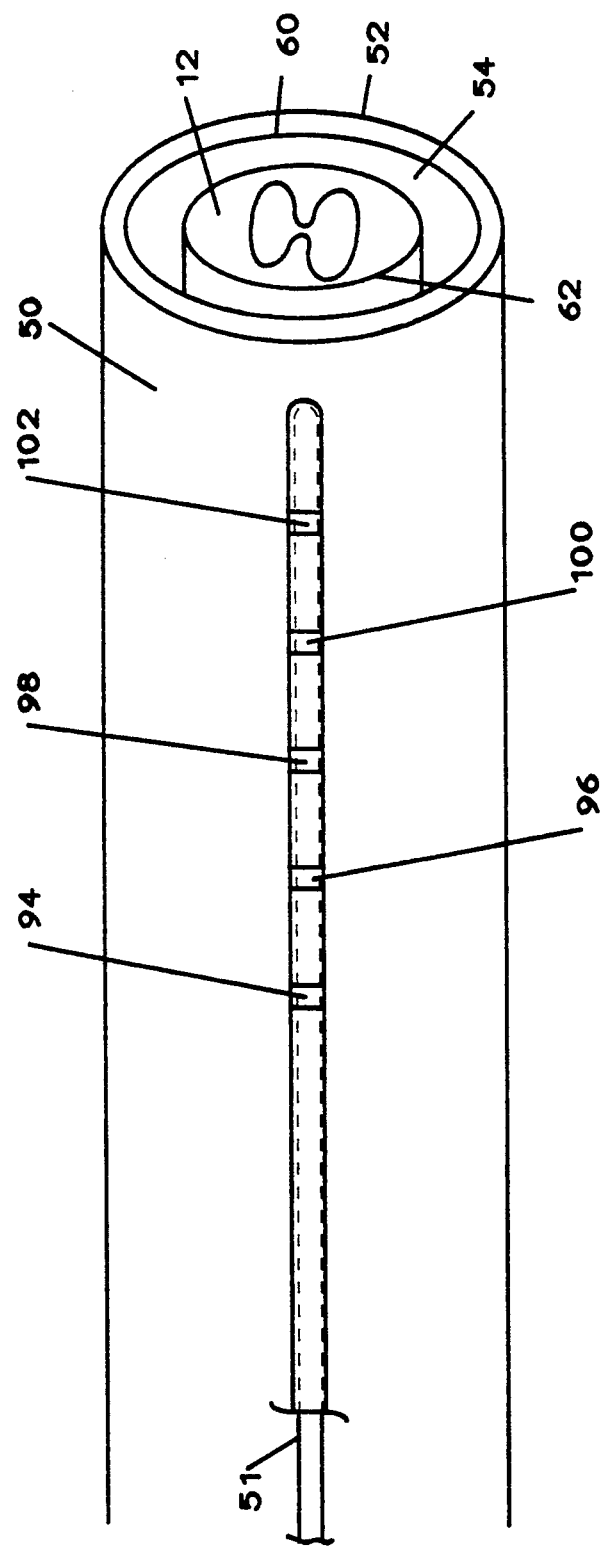
FIG. 4 is a view of the distal end of the insulated neurological lead with straightening stylet inserted into the epidural space; and, FIG. 5 is a conceptual view of the distal end of the insulated neurological lead within the epidural space with straightening stylet removed.

FIG. 4 is a schematic view of the distal end of insulated lead 16 after insertion into epidural space 50. Insertion is accomplished using a straightening stylet 51 shown in partial phantom. The straightening stylet 51 deforms the deformable sigmoidal bend of the distal tip of insulated lead 16 for ease of insertion.

Figure 5:
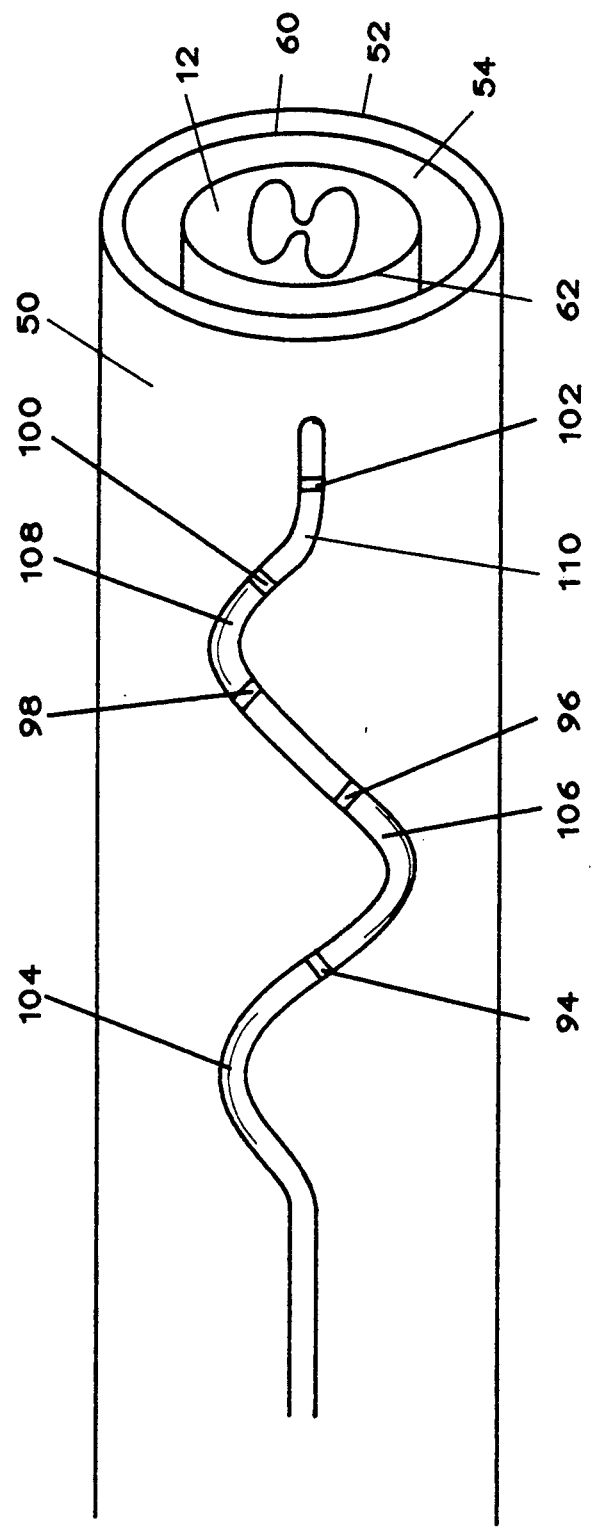

FIG. 5 is a schematic view similar to FIG. 4 after removal of straightening stylet 51. Notice that the sigmoidal shape will tend to maintain the position of the distal end of insulated lead 16.

An important aspect of the present system is that 94, 96, 98, 100, and 102 are thus positioned at different lateral positions within the spinal cord. This means that each lies adjacent to a different longitudinal tract of the spinal cord. Because each of the electrodes is individually coupled to implantable pulse generator 20, stimulation of the desired longitudinal tract(s) is readily affected by selection of the desired electrode(s).

Having thus described the preferred embodiments of the present invention, those of skill in the art will be readily able to apply the teachings found herein to other embodiments within the scope of the claims hereto attached.

We claim:

1. An apparatus comprising:
   a. a neurological pulse generator; and,
   b. an implantable lead coupled to said neurological pulse generator having a sigmoidal deformable shape and having a plurality of electrodes interspersed along said deformable shape.

2. An apparatus according to claim 1 wherein said deformable shape further comprises a deformable sigmoidal bend.

3. An apparatus according to claim 2 further comprising a removable straightening stylet within said implantable lead.

4. In an implantable lead for spinal cord stimulation having an electrode with a distal end and having a sigmoidal shape at said distal end within the epidural space, the improvement comprising:
   a plurality of electrodes interspersed along said sigmoidal shape.

5. An improvement according to claim 4 wherein said plurality of electrodes comprises five electrodes.

6. A method of stimulting a spinal cord of a patient comprising:
   a) performing an insulated lead having a central lumen and having a proximal end and a distal end and having at least one electrode adjacent said distal end such that a region of said distal end resiliently returns to a non-linear shape and said at least one electrode is located within said region;
   b) straightening said region by passing a stylet through said central lumen;
   c) implanting said region within the epidural space of said spinal cord;
   d) removing said stylet; and
   e) electrically coupling said proximal end of said insulated lead to a pulse generator.

7. A method according to claim 6 further comprising: implanting said pulse generator.

8. A method according to claim 7 wherein said performing causes said region to resiliently return to a sigmoidal shape.

9. A method according to claim 8 wherein said at least one electrode is a plurality of electrodes.

10. A method according to claim 9 wherein said plurality of electrodes is five electrodes.

11. A method according to claim 9 which further comprises:
    rotating said region such that after said removing steps, said plurality of electrodes are laterally displaced within said spinal cord.

12. A method according to claim 7 wherein said at least one electrode is a plurality of electrodes.

13. A method according to claim 12 wherein said plurality of electrodes is five electrodes.

14. A method according to claim 12 further comprises:
    rotating said region such that after said removing step, said plurality of electrodes are laterally displaced within said spinal cord.

* * * * *

UNITED STATES PATENT AND TRADEMARK OFFICE
CERTIFICATE OF CORRECTION

PATENT NO. : 5,121,754
DATED : June 16, 1992
INVENTOR(S) : Mullett

It is certified that error appears in the above-indentified patent and that said Letters Patent is hereby corrected as shown below:

Col. 2, line 20, "Fig. is" should be --Fig. 1 is--.

Signed and Sealed this

Twentieth Day of September, 1994

Attest:

BRUCE LEHMAN

*Attesting Officer*     *Commissioner of Patents and Trademarks*